(12) United States Patent
Charron

(10) Patent No.: US 6,260,413 B1
(45) Date of Patent: Jul. 17, 2001

(54) ROTATING DEVICE FOR MEASURING AERODYNAMIC CHARACTERISTICS OF A WALL AND ITS METHOD

(75) Inventor: Yves Charron, Longpont-sur-Orge (FR)

(73) Assignee: Institut Francais Du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/309,577

(22) Filed: May 11, 1999

(30) Foreign Application Priority Data

May 11, 1998 (FR) .................................................. 98 06504

(51) Int. Cl.$^7$ .................................................. G01M 9/00
(52) U.S. Cl. .................................................. 73/147
(58) Field of Search ........................... 73/147, 1.16, 1.34, 73/178 R, 865.6, 866.5, 756; 244/198, 200, 203, 204; 92/89, 90, 93, 96, 97

(56) References Cited

U.S. PATENT DOCUMENTS

| | | |
|---|---|---|
| 4,485,450 | 11/1984 | Characklis et al. .................. 364/550 |
| 4,643,021 | 2/1987 | Mattout ..................................... 73/59 |
| 4,821,564 | 4/1989 | Pearson et al. .......................... 73/155 |
| 5,301,541 | 4/1994 | Joseph et al. ........................ 73/54.32 |
| 5,452,609 | * 9/1995 | Bouis ..................................... 73/147 |
| 5,961,080 | * 10/1999 | Sinha ..................................... 244/204 |

\* cited by examiner

*Primary Examiner*—William Oen
(74) *Attorney, Agent, or Firm*—Antonelli, Terry, Stout & Kraus, LLP

(57) ABSTRACT

The invention relates to a device which determines aerodynamic characteristics of a wall. The device comprises a drum secured to a shaft, an enclosure defining with the drum at least one test zone (10a; 40a), a test fluid delivery line communicating with this test zone and means which determines a parameter representative of the friction factor of the fluid in the at least one test zone. The at least one test zone has a determined width 1 or gap width, for a given rotating speed of the drum and a test fluid having known characteristics (visosity, density . . . ), so that the fluid has a turbulent flow in the vicinity of the wall(s) to be tested, the turbulent flow corresponding to a given Reynolds value Re.

34 Claims, 2 Drawing Sheets

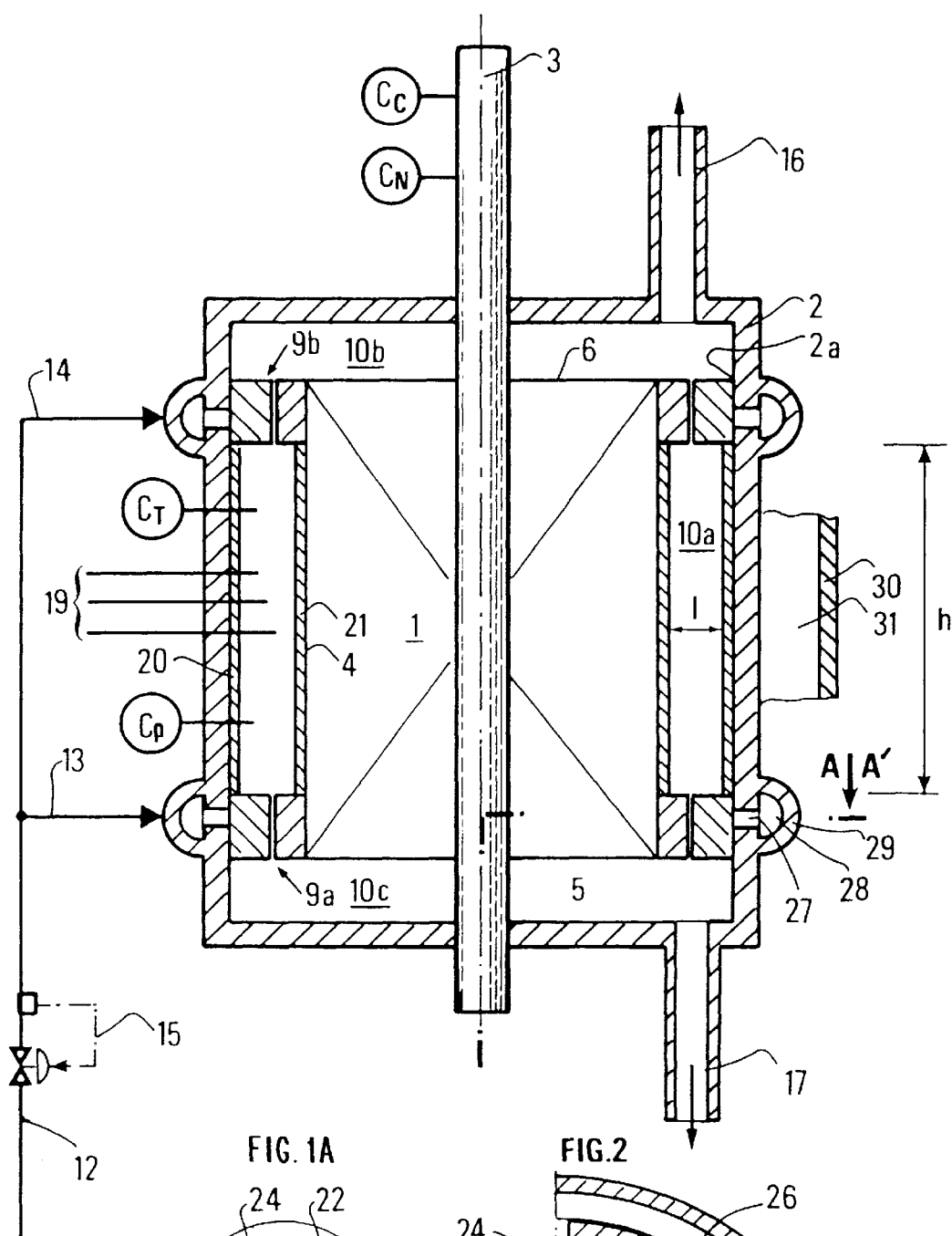
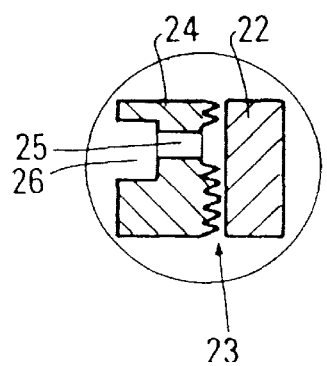
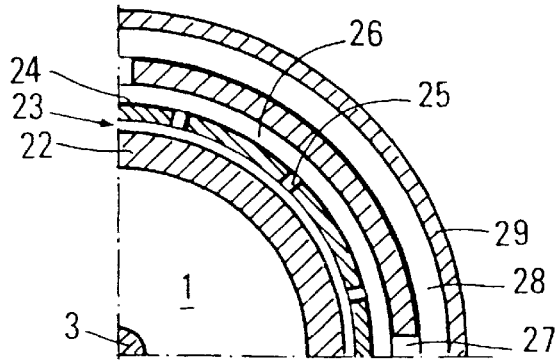

ROTATING DEVICE FOR MEASURING AERODYNAMIC CHARACTERISTICS OF A WALL AND ITS METHOD

BACKGROUND OF THE INVENTION

1. Field of the Invention

The present invention relates to a device and to a method for determining aerodynamic properties or characteristics of a wall in contact with a fluid having turbulent flow.

2. Description of the Prior Art

The prior art describes various ways of evaluating the pressure drop of a pressurized gas on turbulent flow in a pipe.

One of these methods consists in stabilizing a flow over a given length, then in measuring the pressure drop downstream, for example between two points of the pipe, the measuring points being sufficiently far from one another. This requires great pipe lengths, mainly with great Reynolds numbers and, for large-diameter pipes, particularly complex procedures (case of hydraulic tests on furrows for example), considerable testing apparatus (high pressure and flow rate), relatively long testing times and therefore high costs.

Viscometers of the prior art are designed with a different aim. They are in fact used to determine the characteristics of a fluid on laminar flow and not the aerodynamic properties of a wall in contact with a fluid on turbulent flow.

SUMMARY OF THE INVENTION

The present invention relates to a device which to determines aerodynamic characteristics of a wall.

The term wall used in the description hereafter refers to the part used for confinement of a fluid and directly in contact with the flow. It can be, for example, the inner part of an unlined channel, a coating or another fluid covering the inner part of a channel.

The term aerodynamic properties refers to, for example, in the case of a channel or a pipe, the pressure drop or pressure loss caused by a fluid flowing along the wall. In the more general case of a plate or of a wall, the drag caused by the flow along its wall is considered.

This pressure drop or drag depends not only on the flow conditions, but also on the characteristics of the wall. The wall is characterized, according to the case, by its surface state, rough patches for example, its geometric shape such as furrows, or by the presence of a film that covers it or of the material that constitutes it.

The aerodynamic properties or characteristics are established in relation to those of a smooth wall made from a standard material such as a steel for which the friction coefficient on turbulent flow in a rectilinear circular pipe is given by the following formula: $f = 0.316/Re^{0.25}$, Re being the Reynolds number of this flow. Thus, in the case of a wall having a higher friction factor than that corresponding to a smooth wall (case of rough patches with a quasi-random spatial distribution at the wall surface for example), the wall is characterized by an equivalent aerodynamic roughness. In the case of a wall having a lower friction factor than that corresponding to a smooth wall (case of furrows with an organized geometry showing on the wall surface or made from a particular material for example), the wall will be characterized by an aerodynamic efficiency value defined in the description hereafter.

The present invention advantageously applies to the field of transport of pressurized natural gas over long distances in gas pipelines. Pressure drop can reach multiples of ten bars and it is then necessary to recompress the gas at regular time intervals, onshore for example, by means of high-power recompression stations, according to pressure drop, or offshore for example, by means of pipes of large diameter according to pressure drop. Such stations or pipes contribute to increasing production costs. Proper evaluation of the aerodynamic characteristics of the surface state of a transport pipe advantageously allows selection of material forming its inner wall or optimization of the characteristics of its surface geometry to minimize the pressure drop that may be induced.

The device comprises:
- a shaft,
- a drum mounted on the shaft,
- an enclosure in which the drum is positioned so as to define a space and at least one test zone,
- at least one line which delivers a test fluid and commuicates with the test zone, and
- devices which determine a parameter representative of the friction factor of the fluid in the test zone.

The said zone has a determined width 1 or a gap width, for a given rotating speed of the drum and a test fluid having known characteristics (viscosity, density . . . ), so that the fluid has turbulent flow in the vicinity of the wall(s) to be tested, the turbulent low corresponding to a given Reynolds number Re.

The drum is cylindrical over at least part of its height.

The device can comprise suitable seals that are arranged to define three zones, a first high-pressure test zone and two low-pressure zones, these zones being physically separated. The physical separation can be provided by the seals.

At least one of the test fluid delivery lines can be placed in the vicinity of the seals.

According to another embodiment, the seals can be situated in the vicinity of the shaft.

The device can be equipped with devices ($C_p$, $C_r$) which determine the pressure and/or the temperature in the test zone.

It can also comprise Pitot tubes which determine the local velocity of the fluid and deduce the velocity profile in the annular zone.

According to an embodiment, the device comprises a heating and/or cooling system for example.

The invention also relates to a method which determines aerodynamic characteristics of a wall. The method includes:
- a test fluid is fed into the test zone comprising the wall(s) to be tested, the test zone being located between a stationary enclosure and a mobile element,
- the said mobile element is rotated,
- the pressure and the rotating speed of the mobile element are selected so as to obtain the desired Reynolds number,
- the dissipative losses in the enclosure are determined,
- the shear stress and the friction factor are determined,
- the value of the shear stress or that of the friction factor are compared with a set of data obtained from three standard walls for the same value of the Reynolds number as that selected for its characterization, and
- the value of the hydraulic characteristic, such as the hydraulic roughness $\epsilon$ or the aerodynamic efficiency of the wall(s) tested, is determined.

The dissipative losses in the enclosure can be determined in the vicinity of a test zone defined by a seal which defines three zones, a first test zone and two zones.

The device and the method notably find an application for the study of walls of a pipe intended for transport of a pressurized gas.

The device according to the invention has various advantages, some of which are given by way of non limitative example. By measuring the dissipative losses:

in the case of a rough wall in direct contact with the flow, it is possible to determine the value of the friction factor (parameter depending on the Reynolds number) and that of the equivalent aerodynamic roughness (absolute or relative, parameter independent of the Reynolds number), in the case of a rough wall covered with a film-forming element, it is possible to determine the value of the friction factor (parameter depending on the Reynolds umber) and that of the equivalent aerodynamic roughness, in the case of a wall comprising furrows, it is possible to determine the value of the friction factor (parameter depending on the Reynolds number) and that of the hydraulic efficiency of the furrow (parameter defined hereunder), in the case of a wall made of a particular material, it is possible to determine the value of the friction factor (parameter depending on the Reynolds number) and that of the aerodynamic efficiency of the material as defined hereafter.

BRIEF DESCRIPTION OF THE DRAWINGS

Other advantages and features of the device according to the invention will be clear from reading the description hereafter of a non limitative example, with reference to the accompanying drawings wherein:

FIG. 1 is a general view of an embodiment example of a device suited for evaluation of the aerodynamic properties of a wall as defined at the beginning of the description, FIG. 2 shows in detail the seal of the device of FIG. 1, and FIG. 3 schematizes another variant of the device.

DETAILED DESCRIPTION OF THE INVENTION

Figure 3:
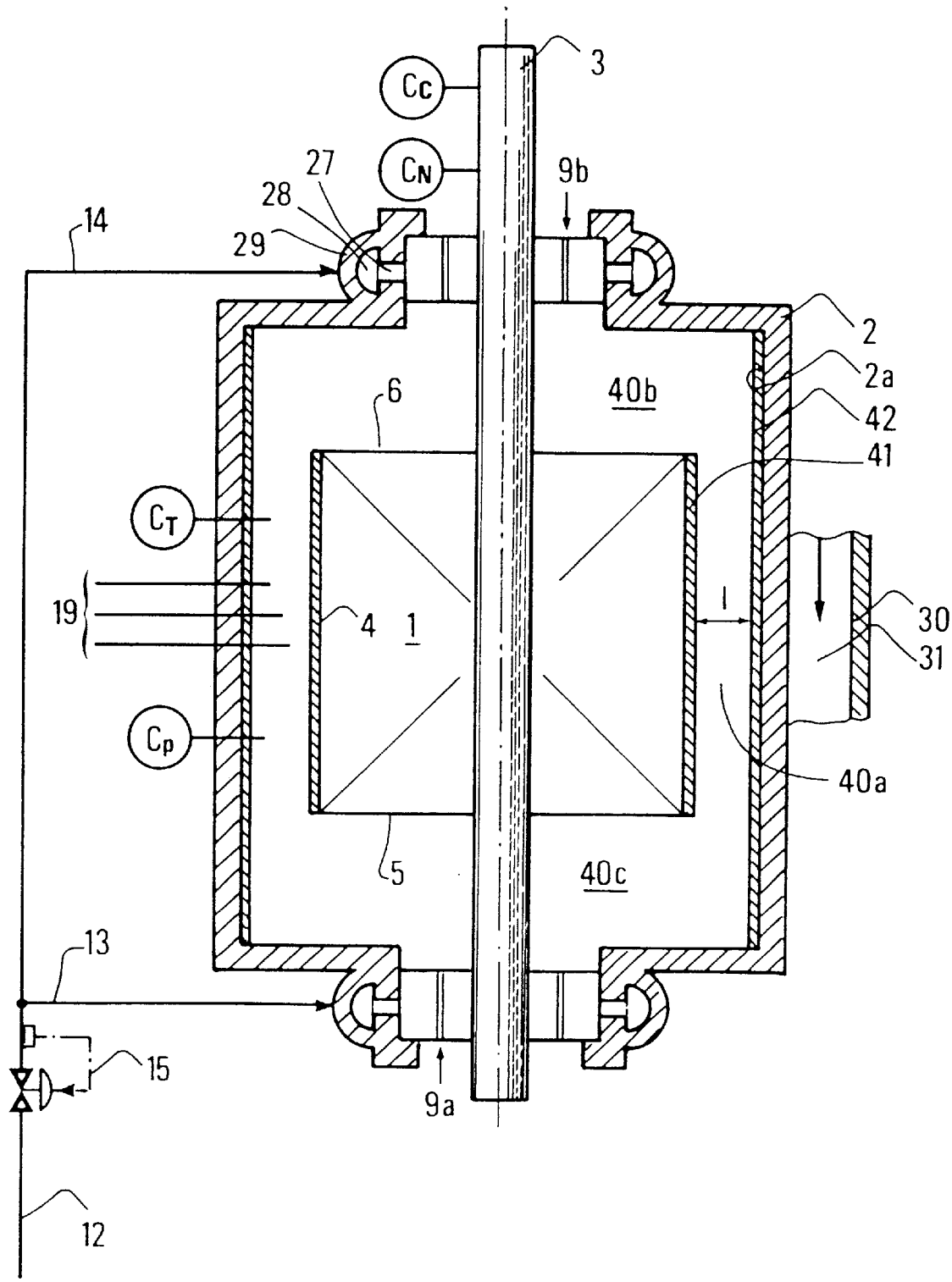

The working principle of the method and of the associated device rotates a drum in an enclosure so as to generate a highly turbulent flow having a Reynolds number greater than $10^6$ for example, and in simulating the flows commonly present in gas pipelines. The drum and the enclosure being moving in relation to one another (rotation), a test fluid under pressure is injected thereafter or simultaneously. The frictions generated by this rotation will generate a torque on the shaft of the device. This torque is measured to determine the aerodynamic properties of the coatings or of the walls in contact with the test gas.

FIG. 1 shows a device which evaluates the aerodynamic properties of the wall of a pipe used for carrying a pressurized gas. A fluid referred to as test fluid, whose aerodynamic properties such as its viscosity and whose thermodynamic properties such as its molecular mass, its compressibility factor are known, is used in order to determine, on turbulent flow, the friction factor and/or the equivalent hydraulic roughness or the hydraulic efficiency of the wall.

The device can be arranged vertically or in any position.

It comprises, for example, a cylindrical drum 1 placed within an external enclosure 2 that is also cylindrical. The drum is mounted on a shaft 3 associated with rotary drive (not shown in the figure) and equipped for example with a speed sensor $C_N$ for measuring the rotating speed N.

Shaft 3 is also associated with device $C_C$ which measures the dissipated energy, a torquemeter for example.

Drum 1 comprises a cylindrical wall 4 having a longitudinal direction parallel to the axis of shaft 3, and two bases 5, 6 referred to as circular walls hereafter, that are substantially perpendicular to the axis of the shaft.

In this example, a space of annular shape is included between the drum and the inner wall 2a of the enclosure. This space has of three zones 10a (high-pressure test zone), 10b and 10c (low-pressure zones). The zones having different pressures are physically separated by seals 9a and 9b placed, in this example, in the vicinity of the two ends of cylindrical wall 4.

Test zone 10a thus corresponds to the annular space contained between inner wall 2a of the enclosure and the outer wall of the drum, and seals 9a, 9b. The detailed view corresponds to seals placed for example in the lower part of the device, seal 9b being symmetrical in relation to seal 9a.

An example of structure of these seals is detailed in FIG. 2.

The gap width 1 of test zone 10a is defined by the radii of the drum and of the enclosure. The latter are selected so as to obtain a gap width 1 capable of generating the desired turbulent flow (and consequently the given Reynolds number Re), considering the characteristics of the test fluid (such as its density $\rho$ and its absolute viscosity $\mu$) and its equivalent velocity of flow Va in the annular zone. This velocity itself depends on the value of the radius and on the rotating speed of the drum.

The hydraulic radius Rh of the test zone is determined as it is known in the art for a non-circular channel, by dividing the surface area s of the annular zone of the test zone by its perimeter p. In the case of a relatively elongate annular zone, for example with a gap height, the part of wall 4 contained between two seals 9a and 9b, that is more than 10 times greater than the width, the hydraulic radius Rh can be considered to be half of the gap width. The hydraulic diameter Dh is defined as twice the hydraulic radius.

The equivalent velocity of flow Va of the fluid in the test zone is determined by means, for example, of the arithmetic mean of the peripheral speeds of the drum and enclosure walls (the latter being zero). It is determined from the rotating speed N measured with device $C_N$.

Another procedure determines this equivalent velocity by taking into account the peripheral speed of the drum walls.

The gap width 1 will thus be determined from the hydraulic radius by means of the following relation: $\frac{1}{2} \approx Rh = (\frac{1}{4}/Va) \ast (Re \ast \mu / \rho)$, Re being the value of the Reynolds number to be simulated.

Zones 10b and 10c correspond to the spaces contained between bases 6, 5 of the drum and the inner wall 2a of enclosure 2. The width of zones 10b and 10c, i.e. the shortest length of the zone, is of the same order as the value of air gap 1.

In FIG. 1, the walls to be tested are situated on the inner wall 2a of enclosure 2, in the vicinity of annular zone 10a and of the outer wall of drum 1. They consist of linings 20 and 21 of length 1c substantially corresponding to the height of the drum decreased by the length of seals 9a or 9b. The walls can have one of the characteristics mentioned at the beginning of the description.

Without departing from the scope of the invention, it is possible to test only one of these two walls, the second wall remaining unchanged during the tests undergone by the first wall.

Enclosure 2 is provided with a gas delivery line 12 that divides into two lines 13 and 14. These lines allow introduction of the test fluid initially and, during the tests, to introduce some test fluid so as to compensate for the gas leaks occurring in the vicinity of the seals 9a, 9b. Pressurized gas delivery line 12 can be equipped with a device 15 providing pressure control by means of a valve.

In the case of labyrinth seal systems known in the art and described in the detailed view and in FIG. 2, test fluid delivery through lines 13 and 14 can be carried out directly in the vicinity of the labyrinths so that no leak occurs near to the test zone. This procedure prevents the turbulent flow within test zone 10a from being disturbed.

The enclosure is also provided with discharge lines 16 and 17 situated close to zones 10b and 10c. All of the gas flowing from the seals systems is thus discharged so as to maintain the pressure as low as possible around zones 10b and 10c. This pressure will preferably be as close as possible to the atmospheric pressure. The pressure in zones 10b and 10c is mainly determined by the diameter of lines 16 and 17. It can also be maintained below the atmospheric pressure by means of an extraction system known in the art, mounted downstream from lines 16, 17 (not shown).

Pressure $C_P$ and temperature $C_T$ detectors are placed near test zone 10a so as to be able to control the temperature and the pressure of the pressurized test fluid which is subject to turbulent flow.

Sealing between the drum and the enclosure can be provided by devices known in the art, for example labyrinth seals, oil-film seals, ring-type seals or seals having self-sealing joints.

The aerodynamic characteristics of a wall are determined from the dissipative losses in test zone 10a. These dissipative losses are for example deduced from the measurement of the transmitted power or of the transmitted torque C and from the rotating speed N, considered near shaft 3 driving drum 1.

The device advantageously comprises external and/or internal heating and/or cooling systems allowing control of the temperature of the fluid in the test zone.

In FIG. 1 for example, this system has a wall 30 surrounding enclosure 2 so as to form an annular space 31. The annular space communicates with an auxiliary source containing a heating or a cooling fluid.

External cooling can for example be provided by a water circuit or by a ventilation device.

Cooling can also be performed internally. A fluid can therefore circulate inside the shaft and inside the drum, the latter being adapted accordingly.

In all the embodiments of the device, it will be possible to have temperature detectors so as to control the cooling system.

FIG. 2 illustrates the details of the seals corresponding to 9a.

The section is taken along section A–A' of the device of FIG. 1. The section comprises a mobile part 22 mounted on the drum wall, a channel 23, a stationary part 24 interdependent with or fastened to the stationary wall 2 of the enclosure. Stationary part 24 is provided with several test fluid delivery and distribution ports 25, an annular channel 26 communicating with these ports.

The wall of enclosure 2 is provided with ports 27 communicating on the one hand with annular channel 26 and, on the other hand, with a line 28 allowing introduction of the test fluid. Reference number 29 represents a bulge in the wall of the enclosure.

The seals shown in detail under reference number 9a are suited to be placed in the lower part of the device. In the vicinity of the upper part, the 9b type seals have a symmetrical shape.

One of the ways for implementing the device and the process allowing the aerodynamic properties of a wall to be determined can comprise the following stages:
Calibration and measuring stages:
  the wall(s) to be tested are mounted, for example lining 21 on the cylindrical outer wall of drum 1 and lining 20 on the inner wall of enclosure 2,
  a gas of a known composition and at a pressure meeting the flow condition requirements is introduced so as to obtain a flow having the desired Reynolds number Re,
  the drum is simultaneously rotated at the required speed to meet the flow condition requirements.
Calibration of the device from known hydraulic characteristics of walls or reference walls The reference walls are preferably made from an uncoated stainless steel comprising rough patches of average amplitude $\epsilon$.

The temperature and the pressure of the test gas in the annular measuring space are measured by detectors $C_T$ and $C_P$.

The Reynolds number Re is determined by the formula as follows:

$$\mathrm{Re} = \frac{2V_A D_H \rho}{\mu} \quad (1)$$

where $V_A$ is the equivalent velocity of flow of the fluid, determined from the measurement of rotating speed N, $D_H$ the hydraulic diameter, $\rho$ and $\mu$ the density and the viscosity of the test gas.

The equivalent shear stress is defined by:

$$\tau = \frac{C_{dis}}{R_{mean} S_{mean}} \quad (2)$$

where $C_{dis}$, $R_{means}$, $S_{mean}$ are respectively:
  the value of the torque corresponding to the dissipative losses of the test zone obtained by the difference between the values of the torques corresponding respectively to the total losses $C_{Tot}$ (valued measured on the shaft) and to the losses outside the annular zone $C_{nan}$ (peripheral zones, bearings, seals),
  the mean gap radius, the surface area developed by the mean gap radius over the height of the test zone.
The friction coefficient is defined by:

$$f = \frac{2\tau}{\rho V_A^2} \quad (3)$$

For a given Reynolds number Re, a torque value or a shear stress value or a friction coefficient value is made to correspond with a surface or reference wall roughness value $\epsilon$. A set of value pairs is established allowing to establish a relation between the roughness measured on the reference wall and any of the previous parameters. The relation can be given in the form of a family of curves, each curve corresponding to a given value Re, in a diagram where the abscissa corresponds to the roughness and the ordinate to the parameter selected, or in the form of an equation.

It is this set of data that will be used as a basis for determining the hydraulic characteristics of a wall from torque measurements as described hereafter.

In the case where two walls having substantially identical or identical characteristics are tested simultaneously, the family of reference curves will be established by taking account of the friction measurements obtained by providing this device with reference walls on the drum and on the inner part of the enclosure, and by following the same procedure as described above.

Measuring stage for establishing the hydraulic characteristics of walls

The reference walls used during the previous stage are replaced by one or two walls arranged as shown in FIG. 1.

The tests are carried out with a Reynolds value for which a roughness calibration is available.

The rotating speed and the torque are measured by means of measuring devices N and torquemeter C.

The shear stress is obtained by means of formula (2), and the friction coefficient by means of formula (3).

The value of the hydraulic roughness coefficient is deduced from the Reynolds number Re, the friction coefficient and the previously constructed set of data (calibration relation by referring either to a set of data relative to the wall or to a set of data established in the case of a test on two identical or at least substantially identical walls, the walls facing each other in the measuring device).

This parameter allows the aerodynamic properties of the wall(s) to be tested.

In some cases, the walls tested have a lower friction factor value $f_S$ than the friction coefficient $f_L$ of a smooth wall made from the reference material.

In such an instance, in the case of furrows for example, a hydraulic wall efficiency value is established by means of the formula as follows:

$$Eff = \frac{f_L}{f_S}$$

Advantageously, it is possible to take account of the dissipative losses in order to determine the aerodynamic characteristics of a wall.

For a device equipped with seals such as that described in FIG. 1, the torque $C_{dis}$ corresponding to the dissipative losses in the annular zone can then be obtained by difference between the values of the torques corresponding respectively to the total losses $C_{Tot}$ (value measured on the shaft) and to the losses outside the annular zone $C_{nan}$ (peripheral zones, bearings, seals). Losses $C_{nan}$ are established by supplying lines 16 and 17 with the test gas, by maintaining the pressure in zones 10b and 10c at the atmospheric pressure, by depressurizing zone 10a (pressure equal to one tenth of the atmospheric pressure for example) and by measuring the torque transmitted to the drum, which is in this case approximately equal to $C_{nan}$.

FIG. 3 schematizes another variant of the device according to the invention where the seals are placed in the vicinity of the shaft. This variant mainly differs from that described in FIG. 1 in that the seals do not separate three zones physically, unlike the device described in FIG. 1.

In this case, the device comprises a single test zone 40a, 40b, 40c that is at the pressure at which the test is carried out.

The linings or walls to be tested, 41 and 42 respectively, are mounted on the cylindrical outer wall of the drum and on the inner wall of the cylinder. Their length substantially corresponds to the height of the drum and to the inner height of enclosure 2.

An example of implementation of this device and of its calibration takes up the stages described above in connection with the device of FIG. 1. Only the total losses $C_{Tot}$ are taken into account to establish the family or families of curves used as a basis for the comparison and to calibrate the device.

Discharge lines 16 and 17 are no longer necessary in this variant since the possible test fluid leaks flow past seals 9a and 9b situated near the shaft.

To sum up, the two variants presented by way of non limitative example can be distinguished as follows:

| FIG. 1 | FIG. 3 |
|---|---|
| Zones 10a, 10b and 10c are "physically" separated by the seals. Zones 10b and 10c are at the atmospheric pressure | Zones 40a, 40b and 40c are not separated by the seals. Zones 40b, 40c are at the testing pressure |
| The width of zones 10b and 10c is of the same order as the gap width | The width of zones 40b and 40c is of the order of some millimeters (1 to 5 for example) for a 125-mm radius drum rotating at 2000 rpm |
| The length of lining 21 = difference between the length of the drum and the height of seal means 9a, 9b | The length of lining 41 = the height of the drum |
| The length of lining 20 = the length of lining 21 | The length of lining 42 = the length of the enclosure considered in relation to the axis of the shaft |
| The family of curves is established from the dissipative loss measurements: $C_{dis} = C_{Tot} - C_{nan}$ | The family of curves is established from the total dissipative losses: $C_{dis} = C_{Tot}$ |
| The test fluid leaks flow through lines 16 and 17 | The test fluid leaks flow through the seal placed near the shaft |
| The test fluid distribution rings 29 are mounted on the largest diameter of the enclosure | The test fluid distribution rings 29 are mounted on the seals placed near the shaft |

Advantageously, the device can also be provided with devices such as Pitot tubes 19 allowing to determine the velocity profile of the pressurized gas on turbulent flow in annular zone or test zone 10a, 40a. It is thus possible to refine the accuracy of calculation by replacing the average velocity value $V_a$ by a representative value obtained from the velocity profile measured.

According to a preferred embodiment, test zone 10a, 40a is cylindrical over the most part of its length, but a drum and an enclosure with any surface of revolution can be used without departing from the scope of the invention.

The devices described in FIGS. 1 to 3 have detachable elements (linings) that can be mounted on the outer part of the drum and/or the inner part of the enclosure for wall testing.

These walls will be equipped with elements known in the art for holding the material or the wall(s) studied in position.

The device may be modular; it may thus be possible to vary the value of the gap width by adding a disk positioned around the drum. This disk can be fastened in the vicinity of the drum or of the shaft.

The device according to the invention advantageously allows determination of aerodynamic properties of walls as identified hereafter by way of non limitative example: furrows, rough patches, a machined, corroded, coated surface, gel or liquid on the wall, irregularities, . . . .

The device can also be provided with a line (not shown in the figures) allowing injection of products or additives that can settle on the wall and alter the aerodynamic properties of the wall.

What is claimed is:

1. A device for determining aerodynamic characteristics of at least one wall, comprising:
   a shaft;
   a drum mounted on the shaft;
   an enclosure in which the drum is positioned so as to define a space including at least one test zone;
   at least one test fluid delivery line communicating with the at least one test zone;
   at least one device allowing determination of a parameter representative of a friction factor of the fluid in test zone; and wherein
   the test zone has a determined dimension for a given rotating speed of the drum and the test fluid having known characteristics, so that the test fluid is subjected to turbulent flow in a vicinity of at least one wall to be tested with the turbulent flow having a given Reynolds number Re.

2. A device as claimed in claim 1, wherein:
   the drum is cylindrical over at least part of a height thereof.

3. A device as claimed in claim 1, comprising:
   a seal defining three zones with the three zones being a first high-pressure test zone and two low-pressure zones.

4. A device as claimed in claim 2, comprising:
   a seal defining three zones with the three zones being a first high-pressure test zone and two low-pressure zones.

5. A device as claimed in claim 3, wherein:
   at least one of the at least one test fluid delivery line is located in a vicinity of the seal.

6. A device as claimed in claim 4, wherein:
   at least one of the at least one test fluid delivery line is located in a vicinity of the seal.

7. A device as claimed in claim 1, comprising:
   a seal positioned in a vicinity of the shaft.

8. A device as claimed in claim 1, comprising:
   at least one measuring device which determines at least one of pressure and temperature in a vicinity of the at least one test zone.

9. A device as claimed in claim 2, comprising:
   at least one measuring device which determines at least one of pressure and temperature in a vicinity of the at least one test zone.

10. A device as claimed in claim 3, comprising:
    at least one measuring device which determines at least one of pressure and temperature in a vicinity of the at least one test zone.

11. A device as claimed in claim 4, comprising:
    at least one measuring device which determines at least one of pressure and temperature in a vicinity of the at least one test zone.

12. A device as claimed in claim 5, comprising:
    at least one measuring device which determines at least one of pressure and temperature in a vicinity of the at least one test zone.

13. A device as claimed in claim 6, comprising:
    at least one measuring device which determines at least one of pressure and temperature in a vicinity of the at least one test zone.

14. A device as claimed in claim 7, comprising:
    at least one measuring device which determines at least one of pressure and temperature in a vicinity of the at least one test zone.

15. A device as claimed in claim 1, comprising:
    a detector which determines a velocity of the test fluid to deduce a velocity profile in the at least one text zone.

16. A device as claimed in claim 2, comprising:
    a detector which determines a velocity of the test fluid to deduce a velocity profile in the at least one text zone.

17. A device as claimed in claim 3, comprising:
    a detector which determines a velocity of the test fluid to deduce a velocity profile in the at least one text zone.

18. A device as claimed in claim 4, comprising:
    a detector which determines a velocity of the test fluid to deduce a velocity profile in the at least one text zone.

19. A device as claimed in claim 5, comprising:
    a detector which determines a velocity of the test fluid to deduce a velocity profile in the at least one text zone.

20. A device as claimed in claim 6, comprising:
    a detector which determines a velocity of the test fluid to deduce a velocity profile in the at least one text zone.

21. A device as claimed in claim 7, comprising:
    a detector which determines a velocity of the test fluid to deduce a velocity profile in the at least one text zone.

22. A device as claimed in claim 1, comprising:
    at least one of a heating and cooling system which controls a temperature of the test fluid in the enclosure.

23. A device as claimed in claim 2, comprising:
    at least one of a heating and cooling system which controls a temperature of the test fluid in the enclosure.

24. A device as claimed in claim 3, comprising:
    at least one of a heating and cooling system which controls a temperature of the test fluid in the enclosure.

25. A device as claimed in claim 4, comprising:
    at least one of a heating and cooling system which controls a temperature of the test fluid in the enclosure.

26. A device as claimed in claim 5, comprising:
    at least one of a heating and cooling system which controls a temperature of the test fluid in the enclosure.

27. A device as claimed in claim 6, comprising:
    at least one of a heating and cooling system which controls a temperature of the test fluid in the enclosure.

28. A device as claimed in claim 7, comprising:

at least one of a heating and cooling system which controls a temperature of the test fluid in the enclosure.

29. A method for determining aerodynamic characteristics of at least one wall comprising:

introducing a test fluid in a test zone comprising the at least one wall to be tested, the test zone being positioned between a stationary enclosure and a mobile element;

rotating the mobile element;

selecting a pressure and rotating speed of the mobile element to obtain a desired Reynolds number;

determining dissipative losses in the enclosure;

determining a shear stress and a friction factor;

comparing a value of the shear stress or the friction factor to a set of data established from reference walls for the selected Reynolds number; and determining a value of an aerodynamic characteristic of the tested at least one wall.

30. A method in accordance with claim 29 wherein:

the characteristic is aerodynamic roughness of the tested at least one wall.

31. A method in accordance with claim 29 wherein:

the characteristic is aerodynamic efficiency of the tested at least one wall.

32. A method as claimed in claim 29, wherein:

the dissipative losses are determined in the enclosure in a vicinity of the test zone defined by seals defining three subzones, a first subtest zone being of a higher pressure and two subtest zones being of a lower pressure.

33. A method in accordance with claim 27 comprising:

testing a wall of a pipe to be used to carry pressurized gas with the device.

34. A method in accordance with claim 31 wherein:

the at least one wall is in a pipe to be used to carry pressurized gas.

* * * * *